United States Patent [19]

Erwin et al.

[11] Patent Number: 4,948,975

[45] Date of Patent: Aug. 14, 1990

[54] QUANTITATIVE LUMINESCENCE IMAGING SYSTEM

[75] Inventors: David N. Erwin; Johnathan L. Kiel, both of San Antonio, Tex.; Charles R. Batishko, West Richland; Kurt A. Stahl, Richland, both of Wash.

[73] Assignee: The United States of America as represented by the Secretary of the Air Force, Washington, D.C.

[21] Appl. No.: 241,992

[22] Filed: Sep. 8, 1988

[51] Int. Cl.$^5$ .............................................. G01N 21/76
[52] U.S. Cl. .............................. 250/361 C; 250/458.1; 422/52
[58] Field of Search ............ 250/361 C, 361 R, 458.1, 250/459.1, 461.1, 461.2, 484.1 A, 337; 436/172; 422/52

[56] References Cited

U.S. PATENT DOCUMENTS

| Re. 28,940 | 8/1976 | Komline et al. | 235/151.31 |
| 3,933,488 | 1/1976 | Noguchi et al. | 250/458.1 |
| 4,128,340 | 12/1978 | Fender et al. | 356/218 |
| 4,193,963 | 3/1980 | Bruening et al. | 422/62 |
| 4,396,579 | 8/1983 | Schroeder et al. | 436/135 |
| 4,435,509 | 3/1984 | Berthold et al. | 436/518 |
| 4,529,855 | 7/1985 | Fleck | 219/10.55 D |
| 4,537,861 | 8/1985 | Elings et al. | 356/317 |
| 4,575,433 | 3/1986 | Spurlin et al. | 252/700 |
| 4,770,478 | 9/1988 | Cross et al. | 350/6.4 |
| 4,791,310 | 12/1988 | Honig et al. | 250/458.1 |

FOREIGN PATENT DOCUMENTS

| 194132 | 9/1986 | European Pat. Off. | 250/361 C |
| 2483117 | 1/1981 | France | 250/484.1 A |
| 8000188 | 2/1980 | World Int. Prop. O. | 250/361 C |

OTHER PUBLICATIONS

Kiel, "Microwave Effects on Immobilized Peroxidase Chemiluminescence", Bioelectromagnetics 4, pp. 193-204, 1983.
Kiel, "Gel State Chemiluminescence: An Artificial Electron Transport System", 4th Intern. Congress on Oxygen Radicals, U. of California at San Diego, Jun. 27-Jul. 3, 1987.
Wong et al., "Anamnestic Chemiluminescence of Murine Spleen Cells", Immunological Communications, 13 (3), pp. 285-290, 1984.
Kiel et al., "Physiologic Aging of Mature Porcine Erythrocytes: Effects of Various Metabolites, Antime- (List continued on next page.)

Primary Examiner—Carolyn E. Fields
Attorney, Agent, or Firm—Bernard E. Franz; Donald J. Singer

[57] ABSTRACT

The QLIS images and quantifies low-level chemiluminescent reactions in an electromagnetic field. It is capable of real time nonperturbing measurement and simultaneous recording of many biochemical and chemical reactions such as luminescent immunoassays or enzyme assays. The system comprises image transfer optics, a low-light level digitizing camera with image intensifying microchannel plates, an image process or, and a control computer. The image transfer optics may be a fiber image guide with a bend, or a microscope, to take the light outside of the RF field. Output of the camera is transformed into a localized rate of cumulative digitalized data or enhanced video display or hard-copy images. The system may be used as a luminescent microdosimetry device for radiofrequency or microwave radiation, as a thermal dosimeter, or in the dosimetry of ultra-sound (sonoluminescence) or ionizing radiation. It provides a near-real-time system capable of measuring the extremely low light levels from luminescent reactions in electromagnetic fields in the areas of chemiluminescence assays and thermal microdosimetry, and is capable of near-real-time imaging of the sample to allow spatial distribution analysis of the reaction. It can be used to instrument three distinctly different irradiation configurations, comprising (1) RF waveguide irradiation of a small Petri-dish-shaped sample cell, (2) RF irradiation of samples in a microscope for the microscopie imaging and measurement, and (3) RF irradiation of small to human body-sized samples in an anechoic chamber.

5 Claims, 11 Drawing Sheets

OTHER PUBLICATIONS tabolites; and Physical Stressors," Am. J. Vet. Res, 47 (10), pp. 2155–2160, Oct. 1986.

Kiel et al., "Metabolic Effects of Microwave Radiation and Convection Heating on Human Mononuclear Leukocytes", Physiological Chem. and Phys. and Med. NMR., 18, pp. 181–187, 1986.

Kiel et al., "Thermochemiluminescent Assay of Porcine, Rat, and Human Erythrocytes for Antioxidative Deficiencies", Anal. Biochem., 143, pp. 231–236, 1984.

Kiel et al., "Microwave Radiation Effects on the Thermally Driven Oxidase of Erythrocytes", Int. J. Hyperthermia, 2 (2), pp. 201–212, 1986.

Datacube brochure for SP-123 Video Bandwidth Signal Processor, Datacube Inc, Peabody, Mass., undated.

Brochure for Video Graphics Module Model QVG-123 with AF123A Expansion, Datacube Inc., Peabody, Mass., undated.

Brochure for Video Input/Output Software (CMOS), Process Software Corp, Amherst, Mass., undated.

Grodzinsky et al., "Electric Field Control of Membrane Transport and Separations", Separation & Purification Methods, 14 (1), pp. 1–40, 1985.

Nussbaum et al., "Proton Diffusion Reaction in a Protein Polyelectrolyte Membrane and the Kinetics of Electro-Mechanical Forces", J. Membrane Sci., 8, pp. 193–219, 1981.

Guy et al., "Circularly Polarized 2450-MHz Waveguide System for Chronic Exposure of Small Animals to Microwaves", Radio Sci., 14 (65), pp. 63–74, Nov.–Dec. 1979.

Price et al., "*Campylobacter pyloridis* in Peptic Ulcer Disease; Microbiology, Pathology, and Scanning Electron Microscopy", Gut, 26, pp. 1183–1188, 1985.

Stewart et al., "Enzyme-Linked Immunosorbant Assay for *Campylobacter pyloriodis*: Correlation with Presence of *C. pyloridis* in the Gastic Mucosa", J. Infectious Diseases, ISS (3), pp. 488–494, 1987.

Beutler et al., "Cachectin: More Than a Tumor Necrosis Factor", New-Eng. J. Med., 316 (7), pp. 379–385, Feb. 1987.

Kelly et al., "Enzymatic Synthesis of Deoxyribonucleic Acid", J. Biological Chem., 245 (1), pp. 39–45, Jan. 1970.

Maniatis et al., "Nucleotide Sequence of the Rightward Operator of Phage $\lambda$", Proc. Nat Acad. Sci., U.S.A., 72 (3), pp. 1184–1188, Mar. 1975.

Rigby et al., "Labeling Deoxyribonucleic Acid to High Specific Activity in Vitro by Nick Translation with DNA Polymerase I", J. Mol. Biol., 173, pp. 237–251, 1977.

Feinberg et al., "A Technique for Radiolabeling DNA Restriction Endonuclease Fragments to High Specific Activity", Anal. Biochem., 132, pp. 6–13, 1983.

Enhancing Real-Time Perception of Quantum Limited Images from a Doubly Intensified SIT Camera System—Wampler, May 85, Academic Press, Inc.

The Study of Epithelial Function by Quantitative Light Microscopy, Spring, 1985, European Journal of Physiology.

The Use of an Imaging Photon Detector in the Simultaneous, Rapid Determination of Multiple Chemiluminescent and Bioluminescent Reactions in Microlitre Volumes, Leaback and Hooper, Coralab Research, Cambridge, England.

Construction of Instrumentation for Bioluminescence and Chemiluminescence Assays, Anderson, Faine, and Wampler, 1978, Academic Press, Inc.

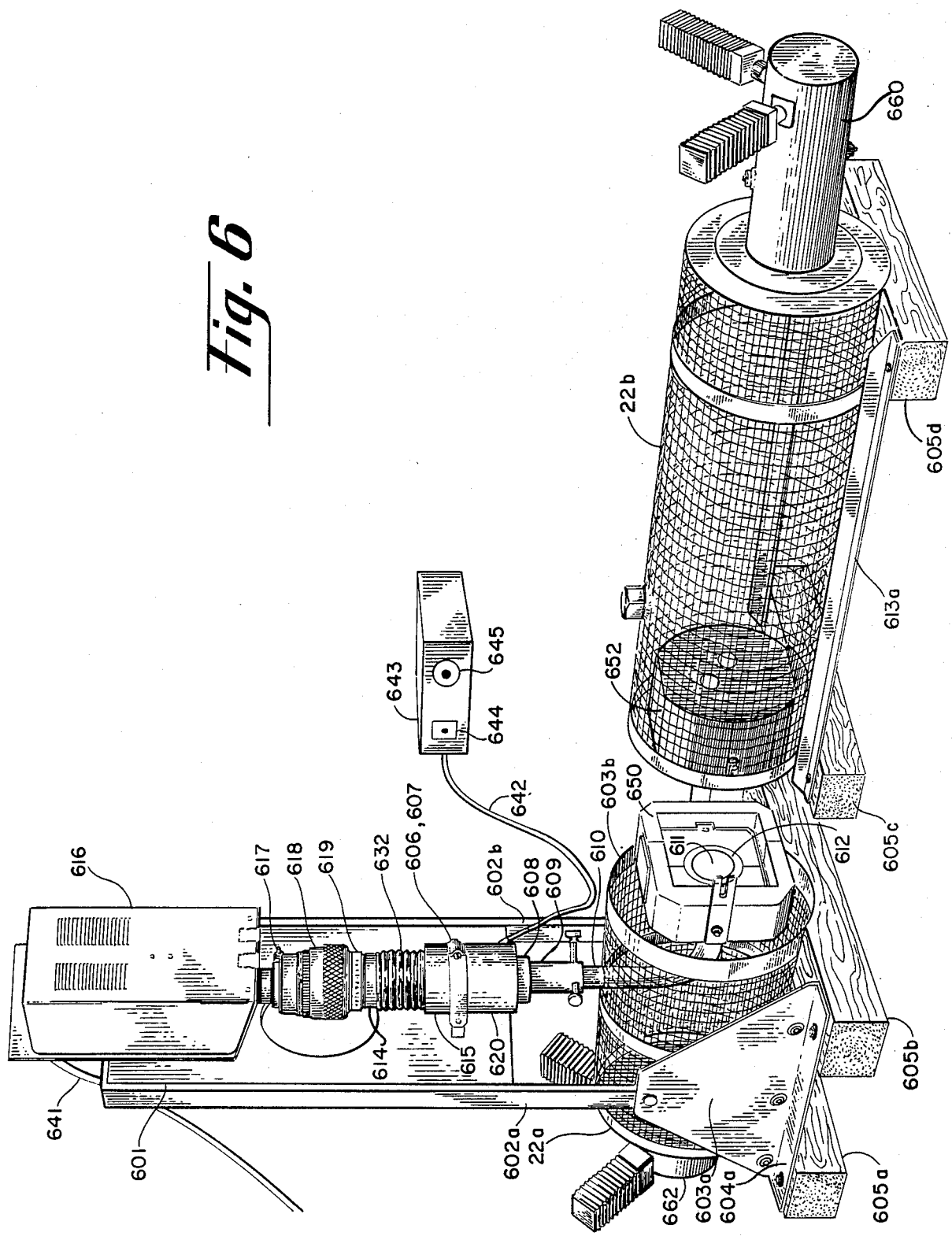

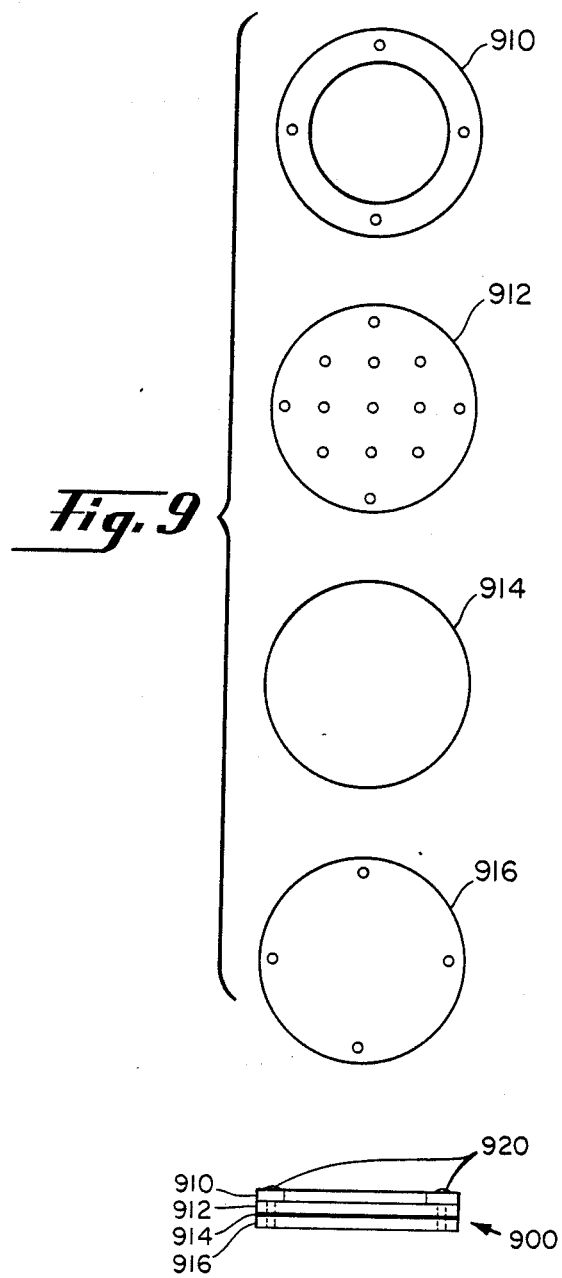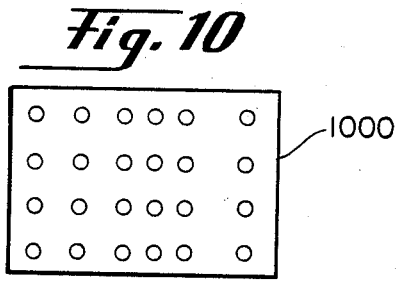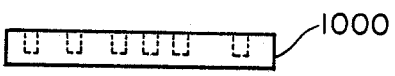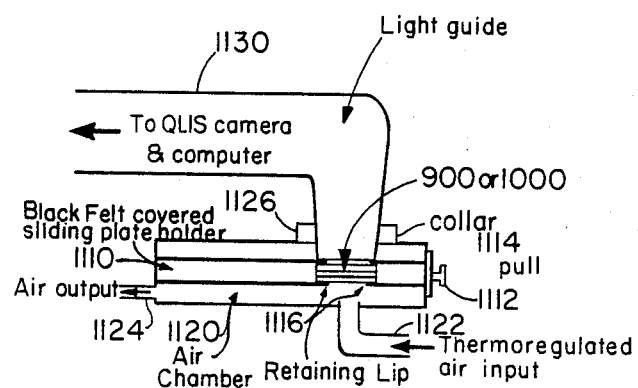

AMBIENT SCAN OF HBO2/GLUCOSE OXIDASE

AMBIENT SCAN OF HBO2 GHP GLUCOSE OXIDASE (W. & W/O AIR)

QUANTITATIVE LUMINESCENCE IMAGING SYSTEM

RIGHTS OF THE GOVERNMENT

The invention described herein was made with Government support under contract DE-AC06-76RLO 1830 aWarded by the Department of Energy and may be manufactured and used by or for the Government of the United States for all qovernmental purposes without the payment of any royalty.

BACKGROUND OF THE INVENTION

The present invention relates generally to quantitative luminescence imaging systems (QLIS) and more particularly to systems for quantitative measurement of low level luminescent reactions in electromagnetic fields in the areas of chemiluminescence assays and thermal microdosimetry.

Luminescent enzymic and immunoassays that require quantitative measurement of low level luminescent reactions in electromagnetic fields are described in copending U.S. applications by J. L. Kiel, Ser. No 06/652,856 titled "Microchemiluminescent Assay System", and Serial No. 06/804 819 titled "Method of Prevention of Oxidative Injury". In the past the measurements were taken by transferring a sample from an RF waveguide in which it is irradiated to a luminometer in which the luminescence is measured using a photomultiplier tube. A principal disadvantage of this method is the relatively long elapsed time between the irradiation of the sample and its measurement in the luminometer.

U.S. patents of interest include No. 4,575,433 to Spurlin et al, which discloses a chemiluminescent cell 10 used to monitor industrial reactions which might be poisoned by sulfide and which involve the emission of photons The system as shown in FIG. 4 of the patent comprises a photomultiplier tube (PMT) and a counter for producing a digital output. Pat. No. 4,193,963 to Bruening et al is concerned with a process and detector for determining organic and inorganic chemical substances in qualitative and quantitative ways by chemiluminescence with ozone. An optical system for viewing the reaction comprises a filter, a photomultiplier tube 17, a data converter 22 and a recorder 23. Pat. No. 4,435,509 to Berthold et al discloses using chemiluminescence in immunoassay processes involving the measurement of light emission In FIG. 1B of Pat. No RE 28,940 to Komline, Sr. et al an electrophoresis cell 22 is viewed using a lens 28, video scanner 44 and computer 36. Pat. No. 4,529,855 to Fleck shows a radiation detector for use in a microwave oven. It comprises a microwave-responsive gas mixture in a sealed container that sustains a white glow to provide a positive indication that the microwave oven is in operation. Pat. No. 4,128,340 to Fender et al discloses a low light level viewing system that includes an image intensifier 10 and eye piece 12

SUMMARY OF THE INVENTION

A principal objective of the invention is to provide a near-real-time system capable of measuring the extremely low light levels from luminescent reactions in electromagnetic fields in the areas of chemiluminescence assays and thermal microdosimetry.

Another objective is to provide a system which is capable of near-real-time imaging of the sample to allow spatial distribution analysis of the reaction.

Also, it is desirable to instrument three distinctly different irradiation configurations, comprising:
1. RF waveguide irradiation of a small petri-dish-shaped sample cell.
2. RF irradiation of samples in a microscope for the microscopic imaging and measurement.
3. RF irradiation of small to human body-sized samples in an anechoic chamber.

The invention relates to a system for imaging and quantifying low-level chemiluminescent reactions in an electromagnetic field It is capable of real time nonperturbing measurement and simultaneous recording of many biochemical and chemical reactions such as luminescent immunoassays or enzyme assays. The Quantitative Luminescence Imaging System (QLIS) in one embodiment is composed of a fiber image guide, a low-light level digitalizing camera with image intensifying microchannel plates, an image processor, and a control computer. Output of the camera is transformed into a localized rate of cumulative digitalized data or enhanced video display or hard copy images. The system may be used as a luminescent microdosimetry device for radio frequency or microwave radiation, as a thermal dosimeter, or in the dosimetry of ultra-sound (sonoluminescence) or ionizing radiation.

BRIEF DESCRIPTION OF THE DRAWING

FIGS. 2 and 3 are symbolic diagrams showing respective embodiments of the invention in a macroscopic system and a microscopic system;

FIGS. 3a and 3b are views of an RF antenna/sampler holder for the embodiment of FIG. 3, with FIG. 3a being a longitudinal sectional view taken along lines 3a—3a of FIG. 3b, and FIG. 3a being a cross section view taken along lines 3b—3b of FIG. 3a;

FIG. 6 is a pictorial view of a specific embodiment of the invention similar to that shown in FIG. 2;

FIG. 7 is an exploded view of the image transfer optics of FIG. 6;

FIG. 9 is an exploded view of a customized round plate, with a side view of the assembly shown in FIG. 9A.

FIGS. 10 and 10A are a top and side view of a standard flat bottom microtiter plate 1000;

FIG. 11 is a symbolic view of a thermal control chamber used in the QLIS system;

Figure 1:
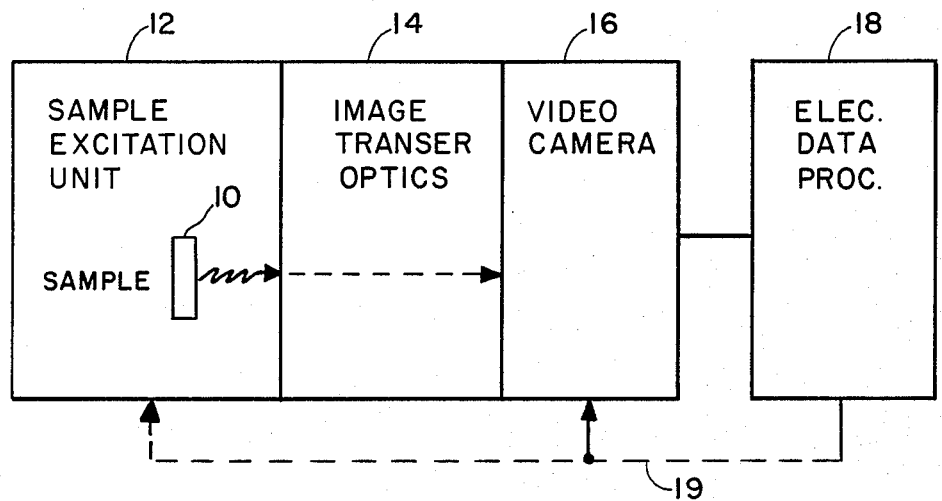
FIG. 1 is an overall block diagram showing a quantitative luminescence imaging system (QLIS) according to the invention.

The file of this application as filed includes four color photographs, three of the apparatus shown in FIGS. 6 & 7, and one of the associated electronic equipment located in an adjacent room

REFERENCES

1. Kiel J. L. Microwave Effects on Immobilized Peroxidase Chemiluminescence Bioelectromagnetics 4: 193-204 (1983).

2. Kiel, J. L. Microchemiluminescent Assay System. U.S. patent application Ser. No. 06/652,856, now abandoned.

3. Kiel, J. L., Simmons, D. M., and Erwin, D. N. Gel State Chemiluminescence An Artificial Electron Transport System 4th International Congress on Oxygen Radicals, 27 June-3 July 1987, University of California at San Diego, La Jolla, Calif. (Platform presentation).

4. Nussbaum, J. H., and Grodzinsky, A. J. Proton Diffusion Reaction in a Protein Polyelectrolyte Membrane and the Kinetics of Electromechanical Forces. Journal of Membrane Science 8 193-219 (1981).

5. Grodzinsky, A. J., and Weiss, A. M. Electric Field Control of Membrane Transport and Separations. Separation and Purification Methods 14: 1-40 (1985).

6. Kiel, J L., Wong, L.S., and Erwin, D. N. Metabolic Effects of Microwave Radiation and Convection Heating on Human Mononuclear Leukocytes physiological Chemistry and Physics and Medical NMR 18: 181-187 (1986).

7. Kiel, J. L., and Erwin, D. N. Physiologic aging of mature porcine erythrocytes: Effects of various metabolites, antimetabolites, and physical stressors American Journal of Veterinary Research 47 2155-2160 (1986).

8. Kiel, J. L., and Erwin, D. N Thermochemiluminescent Assay of Porcine, Rat, and Human Erythrocytes for Antioxidative Deficiencies. Analytical Biochemistry 143: 231-236 (1984).

9. Kiel, J. L., and Erwin, D N. Microwave Radiation Effects on the Thermally Driven Oxidase of Erythrocytes. International Journal of Hyperthermia 2: 201-212 (1986).

10. Guy, A. W. Wallace, J., and McDougall, J. A., Circularly Polarized 2450-MHz Waveguide System for Chronic Exposure of Small Animals to Microwaves, *Radio Science* 14, No. 6S, 63-74, 11. Price, A. B., Levi, J , Dolby J. M., et al. *Campylobacter pyloridis* in peptic ulcer disease: Microbiology, pathology and scanning electron microscopy. Gut 26: 1183-1188 (1985).

12. Goodwin, C. S , Blincow, E., Peterson, G , et al. Enzyme-linked Immunosorbent Assay for *Campylobacter Pyloridis:* Correlation with Presence of *C. pyloridis* in the Gastric Mucosa The Journal of Infectious Diseases 155: 488-494 (1987)

13. Beutler B., and Cerami A. Cachectin More than a Tumor Necrosis Factor The New England Journal of Medicine 316: 379-385 (1987).

14. Kelly, R. B., Cozzarelli, N. R., Deutscher, M. P., Lehman, I. R., and Kornberg, A. Enzymatic Synthesis of Deoxyribonucleic Acid. XXXII. Replication of Duplex Deoxyribonucleic Acid by Polymerase at a Single Strand Break. The Journal of Biological Chemistry 245: 39-45 (1970).

15. Maniatis, T., Jeffrey A., and Kleid, D. G. Nucleotide Sequence of the Rightward Operator of Phage. The Proceedings of the National Academy of Sciences of the United States of America 72: 1184-1188 (1975).

16. Rigby, P. W. J., Dieckmann, M., Rhodes, C., and Berg, P. Labeling Deoxyribonucleic Acid to High Specific Activity in Vitro by Nick Translation with DNA Polymerase I. Journal of Molecular Biology 113 237-251 (1977).

17. Feinberg, A. P., and Vogelstein, B. A. Technique for Radiolabeling DNA Restriction Endonuclease Fragments to High Specific Activity. Analytical Biochemistry 132: 6-13 (1983).

DETAILED DESCRIPTION

Overall System Description

As shown in the block diagram of FIG. 1, the system is comprised of four major components. These are a sample excitation unit 12, image transfer optics 14, a video camera 16 and an electronic data processing system 18. The sample excitation unit 12 provides some means such as irradiation in an RF field for exciting a sample 10 to produce a luminescent reaction The resulting low light level image from the sample 10 is transferred out of the excitation environment by the image transfer optics 14 to the input of the video camera 16. The output of the video camera 16 comprises electric signals which are supplied via a line 17 to the input of the data processing system 18.

Figure 2:
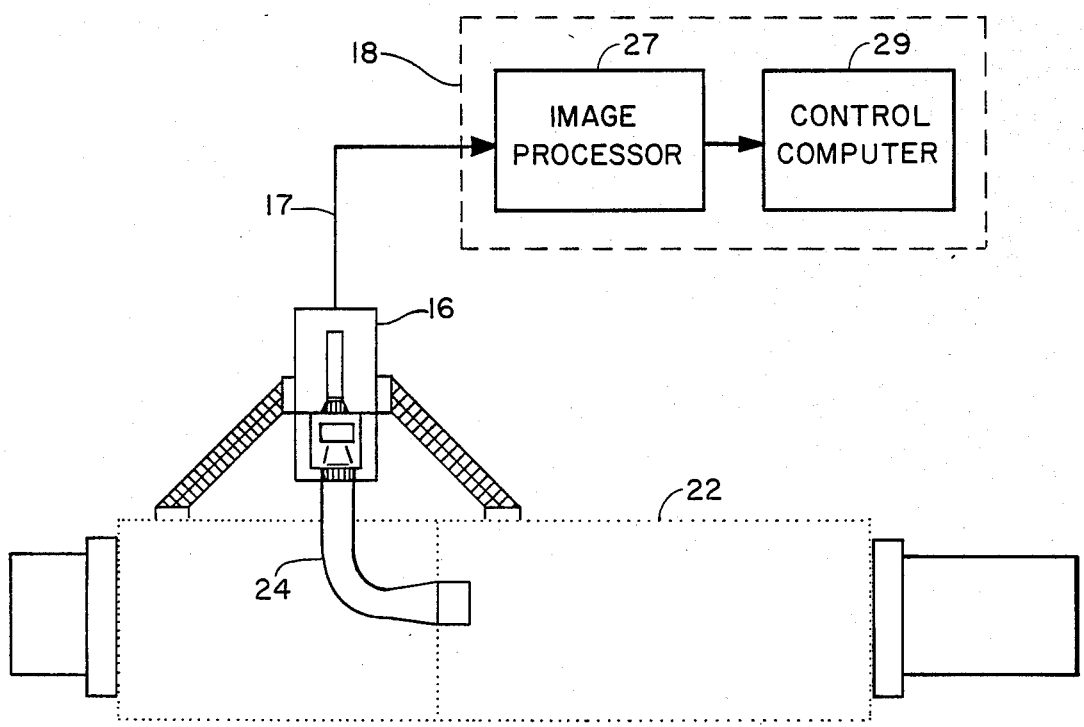

In the macroscopic system shown in FIG. 2, the sample excitation unit is an RF waveguide/sample chamber 22, the image transfer optics is a fiber optic image guide 24, the video camera 16 is a low light level camera, and the data processing system 18 comprises an image processor 27 and a control computer 29.

Thus, the Quantitative Luminescent Imaging System (QLIS) of FIG. 2 is composed of a coherent fiber optic image guide 24 contained in a circularly polarized cylindrical (wiremesh) waveguide 22, a low light level video camera 16 with a 35 mm f/1.4 lens, and an image processor with VIOS software drivers and Datacube boards serviced by a microprocessor (MicroVax II). The QLIS is calibrated With a TLS Systems model #40108-4 solid state scintillator with phosphor #5000 (520 nm emission peak) and a carbon-14 activator of 17.5 milliCuries. The source is held in an adapter which allows the source to be coupled to the input window of the QLIS. The adapter has a sliding shutter to prevent excitation by room light when not in use. The samples examined were held in 1.0×1.0×4.5 cm polyacrylate cuvettes which were, in turn, contained in a polystyrene foam holder (microwave transparent) with one side removed and held against the input window of the QLIS. Temperature was measured in the cuvette during microwave exposure with a nonperturbing electrothermia probe and monitor (Model 101, Vitek).

In the microscope system shown in FIG. 3, the sample excitation unit is an RF antenna/sampler holder 32, shoWn enlarged in FIG. 3A, the image transfer optics is a microscope 34, the video camera 16 is a low light level camera attached to the microscope, and the data processing system 18 (not shown) may be the same as is shown in FIG. 2.

Waveguide/Sample Chamber

The waveguide/sample chamber 22 for the macroscopic configuration of FIG. 2 comprises a circularly polarized wiremesh waveguide 22 tuned to 2450 MHz. It is operated in the $TE_{11}$ and $TM_{11}$ circularly polarized modes. Directional couplers and power meters allow monitoring of input, output, and reflected power. The microwave source is an EPSCO model P65KB (see 10. A. Guy, J. Wallace, J. McDougall, *Radio Science* 14, 65, 1979). The image transfer optics is a coherent fiber optic image guide 24 contained in the waveguide 22.

For the microscope case shown in FIG. 3, the sample excitation unit 32 includes a waveguide (see FIGS. 3A and 3B) in the form of a coaxial cable 31. The end of the cable is opened to form an antenna 33, which provides an RF field with the appropriate spatial distribution for irradiation of the sample. The sample 30 is placed on a microscope slide petri dish, or similar sample holder 30d which allows imaging the material of interest.

The normal components of the microscope 34 include an objective lens 370, a beam splitting prism 372, an eyepiece 374, a transfer optic 376, and a film pack 380 A removable mirror 355 is provided so that without the mirror light goes to the filmpack, and with the mirror the light goes to the camera. Also normally there would be a condenser and other optical elements below the sample location 32. Light from a light source 350 would be directed via a mirror 351 and up through the sample and other optics via a path 35 to the eyepiece or filmpack. Principle image locations are shown at 35a and 35b. The low light level camera 16 is attached to the microscope at a standard mount 378.

For the microscope QLIS system, the RF antenna/sample holder 32 is used at the sample location, and the optical elements below the sample holder are removed to permit the coaxial cable 31 to extend down from the antenna portion and then from the microscope to a radio frequency generator 310. The end of the coaxial cable 31 opened to form the antenna 33 is opaque, and epi-illumination is used to view the sample, except that all illumination is removed to view by chemiluminescence, using the QLIS. The epi-illumination light path 35e is from the light source 350, via mirrors 352 and 354.

FIGS. 3a and 3b are views of the RF antenna/sampler holder 32 and cable 31, with FIG. 3a being a longitudinal sectional view taken along lines 3a—3a of FIG. 3b, and FIG. 3a being a cross section view taken along lines 3b—3b of FIG. 3a. The coaxial cable 31 has an outer conductor 31a, insulation 31b, and a center conductor 31c. At the end of the cable, the outer conductor is expanded to form the antenna 33. The microscope slide, petri dish, or similar sample holder 30d is of a material transparent to the RF energy.

The radio frequency energy from the generator 310 can be any of many frequencies, but would typically be at 2450 MHz for the most common generators, and for aqueous samples such as biological specimens. A typical power level would be a few watts.

Camera

Figure 4:
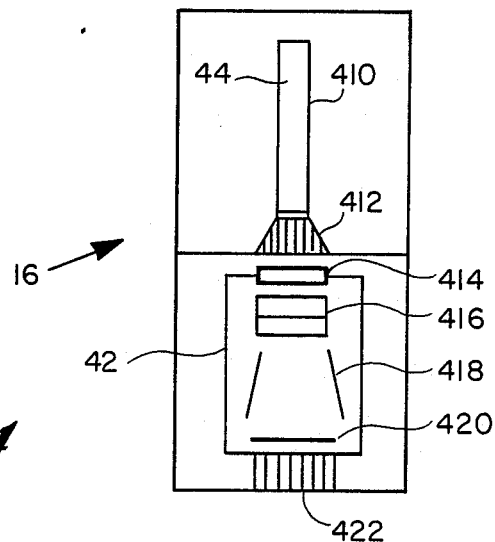
FIG. 4 is a symbolic diagram of a video camera which may be used in either the system of FIG. 2 or the system of FIG. 3.

The video camera 16 is shown in FIG. 4. It comprises a microchannel plate image intensifier 42 optically coupled to a video image tube 44. The symbollic drawing of the camera 16 in FIG. 4 shows a video imaginq tube 410, a fiber optic coupler 412, a phosphor screen 414, microchannel plates 416, focusing electrodes 418, a photocathode 420, and a fiber optic faceplate 422.

This type of camera normally is used for low light level imaging when the illuminance of the object is in the $10^{-6}$ foot-candles range. However, in some instances, a less sensitive type camera would be sufficient The choice of a specific sensitiity, type, and design of camera used on this measurement system is driven by the expected illuminance level of the object, and resolution and image quality requirements. For each set of experimental conditions, one who is skilled in the field of video imaging can choose the particular type and design of camera to best capture the images of interest. With typical sensitivity of $10^{-1}$ foot-candles, the vidicon is considered in the electronic imaging community to be the dividing line between normal and low light level imaging devices. For the present chemiluminescence investigation, a low light level camera such as the image intensifier/video image tube mentioned above will be used. However, cameras such as an ISIT (Silicon Intensified Target), nuvicon, video image tube, CID (Charge Injection Device), CCD (Charge Coupled Device), could be used to better match the source characteristics.

Image Transfer Optics

Figure 5A:
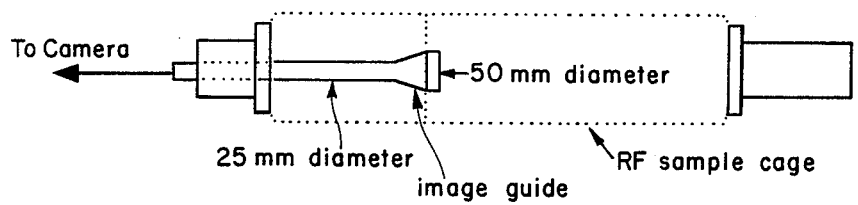
FIGS. 5a, 5b and 5c show possible variations for the image transfer optics.
Figure 5B:
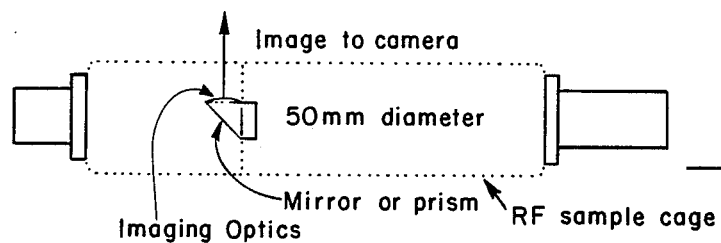
Figure 5C:
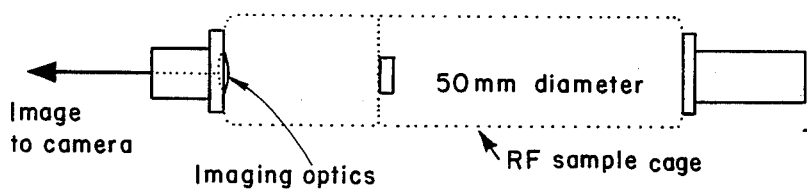

The image transfer optical system 24 for the macroscopic configuration of FIG. 2 is used to transfer the source distribution from the sample plane within the RF flux contained in the waveguide to the input plane of the camera. This eliminates RF interruption of the electronic function of the camera, and disturbances in the RF field distribution caused by the presence of the camera inside the waveguide. The optical system shown in FIG. 2 is a coherent fiber optic bundle 24. The input end of the bundle is in contact with the sample cell and the output end is connected to the input of the camera. The fiber optic bundle 24 may exit through the side of the RF cage (as in FIG. 2) or through the rear (as in FIG. 5a). The taper length, final diameter, and bend radius (for the side exit case) are driven by the configuration of the sample chamber, camera, system layout, and fabrication requirements. Other optional transfer optics systems might include a mirror or prism (provided that no metallic coatings are used) placed behind the sample chamber and combined with imaging optics to bring the image out to the camera, as in FIG. 5b. An alternative image transfer system could transfer the image through the rear portion of the waveguide as in FIG. 5c. The usable configuration of lenses, mirrors, prisms, and fiber-optics are innumerable and subject to special geometrical and sensitivity considerations. One with skills in optical design can choose the optimal image transfer system, taking into account the given experimental conditions.

The image transfer system for the microscope case of FIG. 3 is actually the microscope itself. In this configuration, the RF excitation is brought to the sample via a coaxial antenna, as shown in FIGS. 3a and 3b. The luminescence from the sample is then imaged to the operator's eye and/or the camera 16 by the normal microscope optics. The camera is attached to the microscope's camera port by a standard lens mount, or if needed, a custom mount could easily be fabricated. Alternatively, a fiber optic coupler could be incorporated as with the macroscopic system. A typical microscope should need no major modification for use in the chemiluminescence experiments.

Image processor/Experiment Control Computer

The image processing system 18 for both the macroscopic and microscopic systems is identical and includes hardware and software sufficient to allow video rate (30Hz) image capture, enhancement, and analysis.

Given the characteristics of the image and the particular types of information to be extracted from it, the specific image processing algorithms to be applied will be obvious to those skilled in the image processing field. Such algorithms would likely include but are not limited to frame averaging, frame substraction, convolution, histogram manipulation, filtering, and other noise reduction, image enhancement and analysis techniques. The image processor hardware may be configured as a stand alone system, a peripheral to a host computer, or a board level system which can be plugged directly into the host computer's bus The host computer may be used to automate the experiments to a degree by controlling camera gain settings, RF exposure times, calibration for non-linearities, etc.

SPECIFIC MACROSCOPIC EMBODIMENT

FIG. 6 is a pictorial view of a specific embodiment of a macroscopic system similar to that shown in FIG. 2.

The video camera (corresponding to block 16 of FIG. 1) comprises a vidicon camera 616 (model ITC-510 available from Ikegama Corp.), and an image intensifier 620 (model KS-1380 available from Opelco Corp.) A 35 mm f/1.4 lens 618 (such as one available from Nikon Corp.) is attached by a Nikon to C mount adapter 617 to the video camera 616. A 52 mm lens coupler 619 (available from Nikon Corp ) is coupled between the lens 618 and a rubber bellows 632 (1⅞ inch inside diameter by 3¼ inches long). The bellows 632 is attached to the lens 618 and to the image intensifier 620 via aluminum rings 614 & 615 (each 1⅞ inch O.D., one inch long and ⅜ inch long respectively). An electric cable 641 from the video camera 616 goes to an electronic image processor, and an electric cable 642 supplies power to the image intensifier 620 via a control box 643. The control box has an on/off switch 644 and a gain control 645.

The image transfer optics (corresponding to block 14 of FIG. 1) comprises a fiber optic bundle 610 with a fiber optic reducer 611 at the lower end. A nylon coupler 612 attaches the reducer 611 to the bundle; alternatively, the coupler 612 could be eliminated by permanently attaching the reducer to the bundle with an optical adhesive. The fiber bundle 610 is attached to the image intensifier 620 by a split ring clamp 608 (1½ inch I.D. alum.) and a sleeve 609 (one inch I D. alum.). The fiber optic bundle 610 has a 90° bend . FIG. 7 shows an exploded view of the fiber optic bundle 610, the reducer 611, and the coupler 612.

The mounting structure includes an aluminum plate 601 (19 inch × 10 inch × ¼ inch) to which the low light intensity camera 616 is attached with screws. There is a 5¼ inch diameter hole (adjacent the lens 618) in the plate 601 having its center 8½ inch from the loWer end. The image intensifier 620 is attached with a ½ inch hose clamp 606 and an aluminum block 607 (1¾ inch × 3¼ inch × ½ inch). The block 607 has a semicylindrical vertical trough which extends to ⅜ inch from the back of the block, and to ¼ inch from each side. The block 607 is attached on the back to the plate 601 and the hose clamp 606 is attached to the block 607.

The plate 601 is attached at its longer edges to two aluminum angles 602a & 602b (29 inch × 1 inch × 1 inch), which in turn are attached to aluminum plates 603a & 603b respectively. The plates 603a & 603b are each 8 inches wide at the bottom × 6½ high × ½ inch thick, with the sides vertical for a height of 2 inches, and then tapered at the two sides to a width of 2 inches at the top. The angles 602a & 602b are centered vertically on the plates 603a & 603b respectively. The base of the structure comprises four wood blocks 505a 505b, 505c & 505d (each 15 inch × 3 inch × 3 inch). The plates 603a & 603b are attached at their lower edges to vertical sides of aluminum angles 604a & 604b respectively (each 11 inches × 2 inches × 2 inches × 3/16 inch). Horizontal sides of the angles 604a (extending outward) & 604b (not visible) are attached at the ends of the blocks 605a & 605b. The two blocks 605c & 605d are spaced apart by two aluminum angles 613a & and a corresponding angle 613b not visible at the rear (each 25 ¾ inch × 1 inch × 1 inch, 3/16 inch thick) attached at the ends of the blocks. Each of the four wood blocks 605a–605d has a cylindrical trough at its center, with the trough having a radius of 4 inches extending to 1⅞ inch from the bottom of the block and having a width at the top of 5 ½ inch.

The wiremesh cage comprising the waveguide 22 is divided into two parts 22a and 22b, which are brought together after a sample is inserted.

FIG. 6 also shows a sample holder comprising two parts 650 & 652, with part 650 mounted in the cage part 22a around the end of the image transfer optics 611–612. The sample is separated from the end of the fiber bundle 610 only by a transparent Wall of the sample holder 650. At the righthand end of the cage portion 22b is mounted an RF generator 660, and at the lefthand end of the cage portion 22b is mounted an RF sink 662. A typical RF frequency from the source 660 would be 2450 MHz, at a power level of 10–50 watts.

FIG. 7 is an exploded view of the image transfer optics, showing the dimensions of the fiber optic bundle 610, the fiber optic reducer 611, and the nylon coupler 612. The coupler 612 is shown in a sectional view. These parts are shown assembled in FIG. 6. FIG. 7 shows two of twelve nylon set screws (¼20 × ½). Three of these screws are used to hold the coupler 612 to the fiber optic bundle 610, and three are used for attaching the coupler 612 to the reducer 611. The screws are spaced at 120° around the circumference. Six of these set screws are used to hold the sleeve 609 to the other end of the fiber optic bundle 610.

Figure 7A:
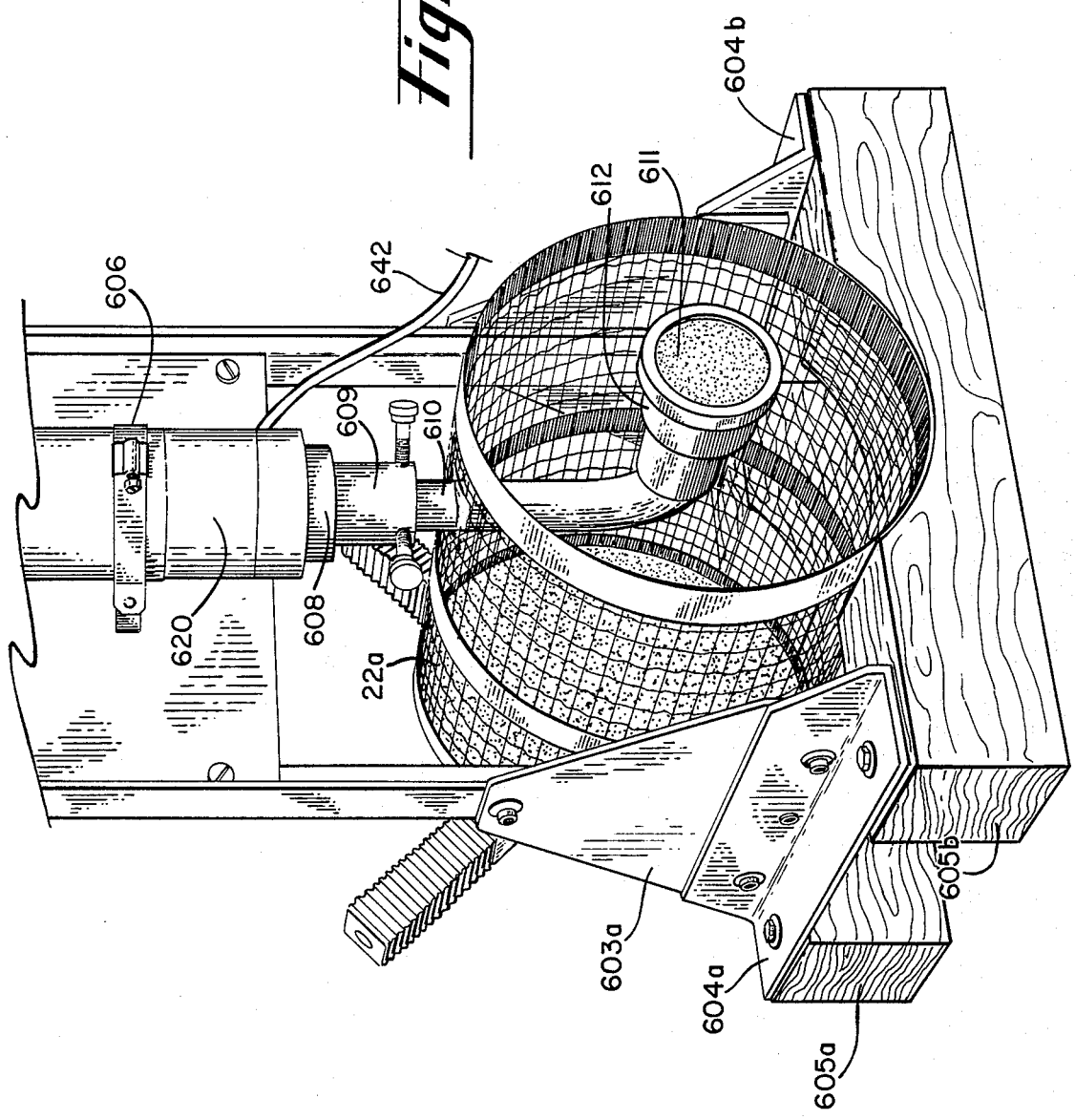
FIG. 7a is an enlarged pictorial view of part of FIG. 6, showing the image transfer optics of FIG. 7 assembled and mounted in the cage portion 22a, with the mounting structure.

FIG. 7a is an enlarged pictorial view of part of FIG. 6, showing the image transfer optics of FIG. 7 assembled and mounted in the cage portion 22a, with the mounting structure. The sample holder 650 is omitted in FIG. 7a.

The Image processor/Experiment Control Computer corresponding to block 18 of FIGS. 1 and 2 comprises an image processor and a host computer.

The Image Processing System—The image processor is a standard off-the-shelf system procured from the Data Cube Corporation. It comprises an SP-123 Video Bandwidth Signal Processor; a Video Graphics Module, Model QVG-123 with AF-123A Expansion; and software from the Process Software Corporation titled for Video Input, Output, & Processing Software with the product name "Video Input/Output Software (VIOS)", for use with Datacube QVG Video Hardware and DEC Computer Systems.

The Host Computer—The VIOS brochure lists several host computers and operating systems available from Digital Equipment Corporation (DEC) which may be used. The experimental Quantitative Luminescent Imaging System (QLIS) makes use of the computer model DEC MicroVAX II with the operating system Micro VMS The image processing system hardware and software is sufficient to allow video rate (30Hz) image capture, enhancement, and analysis. Given the characteristics of the image and the particular types of information to be extracted from it, the specific image processing algorithms to be applied will be obvious to those skilled in the image processing field. Such algorithms would likely include but are not limited to frame averaging, frame subtraction, convolution, histogram manipulation, filtering, and other noise reduction, image enhancement and analysis techniques.

The image processor has no unique features. It has two principal functions in the system: to grab and digitize video frames for processing, and to process them in various ways to enhance the data, either for display purposes or for use in improving the signal-to-noise ratio. Along with the system description and the following information, it would be possible to use either this or an equivalent image processor and integrate it into the system to perform the necessary functions. This is a middle range system.

Image processing System Algorithms—The image processor was delivered with a library of standard image processing functions, including those for frame grab and digitizing, frame averaging, generation of contour displays of gray level, and a variety of others. The library is typical of those provided with lower middle range commercial image processing software. The algorithms are implemented in the purchased software, so that we do not have access to those algorithms.

Our contribution has been to integrate the computer, image processor, and camera. We have written software which accesses the library functions and calibrates the image (See the appendix). Calibration is accomplished by comparison of the digitized values to values acquired using an NBS-traceable light source.

The host computer may be used to automate the experiments in the future to a degree by controlling camera gain settings, RF exposure times, calibration for non-linearities, etc. The technique would be to use a fiber optic device to channel light from a standard source to a small area near the edge of the sample plane so that it is imaged with the sample. Normal operation of the instrument allows monitoring of the image signal from th sample area to determine if a higher or lower signal is desired. Gain is adjusted using a rotary control on the intensifier control box so that automation of this control is easily accomplished by well-known methods. Calibration is maintained by measuring the small area source image and normalizing the calibration.

The control box 643 is shown in FIG. 6. Normal operation is to apply power (using the off/on switch 644 of the control box). then to advance the gain control (rotary knob 645 on the control box) until an image is displayed on the monitor.

OPERATION

The following description illustrates the operation of the QLIS for the purpose of detecting effects of microwave heating on the chemical reaction rate of chemiluminescent reactions.

Luminol, bovine serum albumin (BSA), and horseradish peroxidase were crosslinked with glutaraldehyde to produce gels for use in the QLIS. Saturated Luminol suspension containing 30 mg BSA per ml of pH 6.9 phosphate buffered saline was filtered to remove undissolved luminol. One mg horseradish peroxidase and 20 $\mu$l of 25% glutaraldehyde were added to this solution.

The solution (200 $\mu$l) was then transferred to the filter paper strip (1.0×4.5 cm) and allowed to gel at room temperature (21 to 22° C.). The reaction was stopped after gelling by washing the strip with 0.1M sodium metabisulfite followed by distilled water. The gel was activated by adding 2 ml 0.1N NaOH and 10 $\mu$l 3% $H_2O_2$ to the cuvette containing the gel strip. The strip was against the wall of the cuvette facing the QLIS fiber optic window (see FIG. 6).

Figure 8:
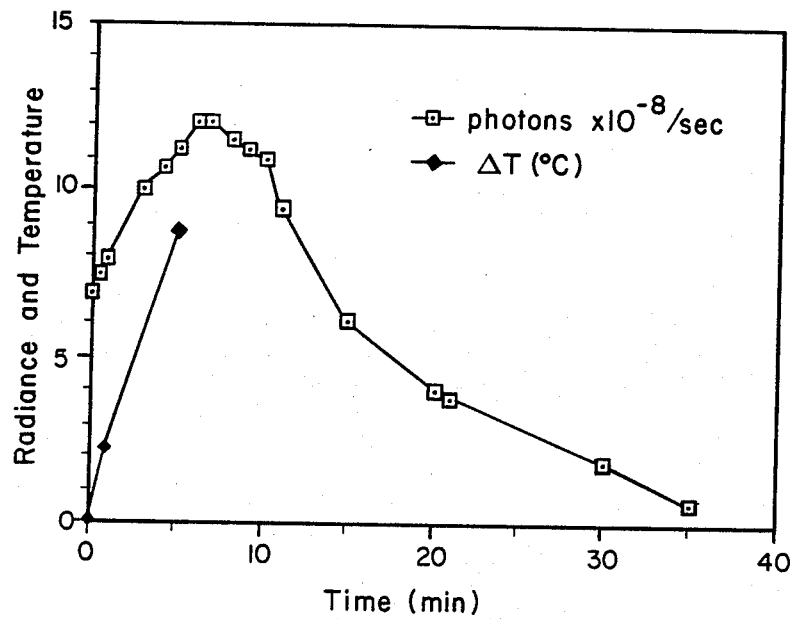
FIG. 8 is a graph showing operational data for QLIS.

See FIG. 8. Luminescent output (white squares) of HRP/Lu-BSA gel filter paper strip (1×2×0.1 cm) activated with 4.4 mM $H_2O_2$ in 0.1N NaOH exposed to 9 watts input of 2450 MHz (4,878 pulses per sec. 5 $\mu$sec pulses) for 10 min intervals (0–10 min and 20 to 30 min). The temperature (black squares) was measured during microwave exposure (beginning at 21° C.). The gel was prepared (as described above) two days before exposure.

Figure 15:
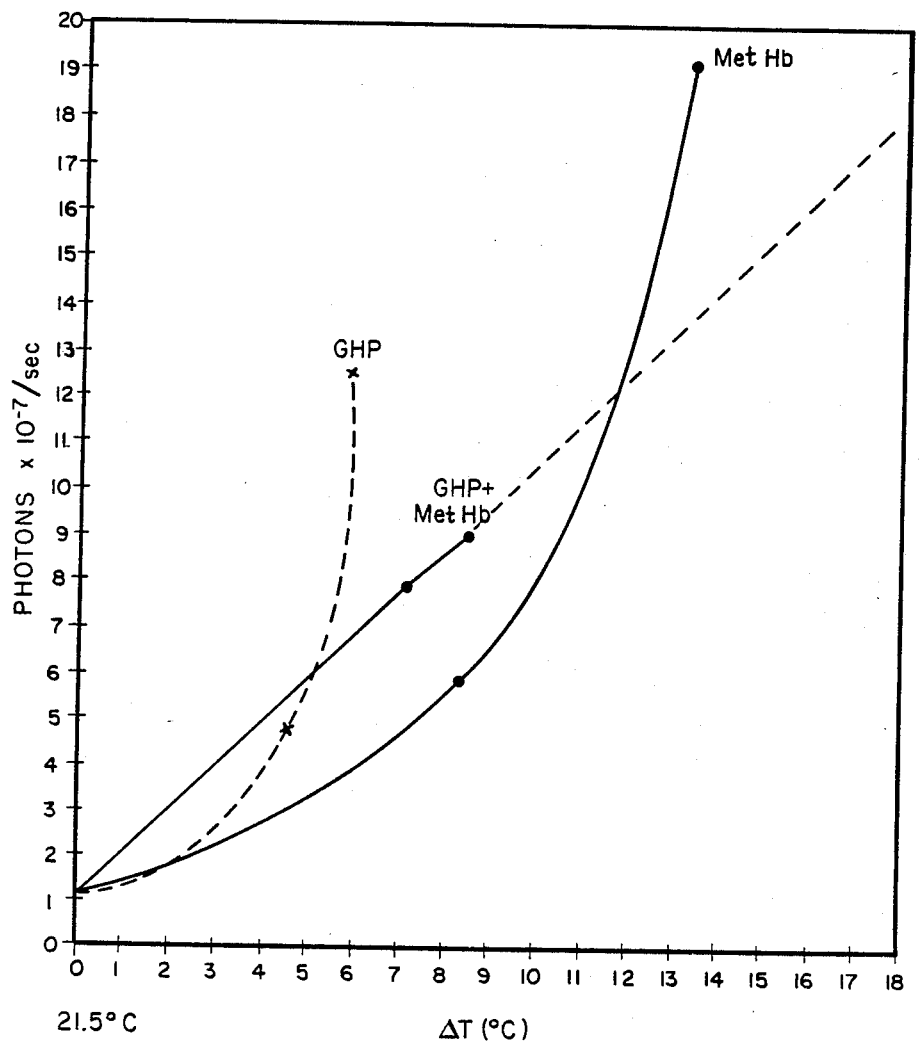
FIG. 15 shows graphs of chemiluminescence for three experiments.

FIG. 15 illustrates results using chemiluminescent gels in which GHP and/or methoglobin were substituted for HRP.

APPLICATIONS OF THE QUANTITATIVE LUMINESCENCE IMAGING SYSTEM

The applications described in this section make use of apparatus as shown in FIGS. 9–12. FIGS. 10 and 10A are a top and side view of a standard flat bottom microtiter plate 1000 which may have 24, 46 or 96 wells, 24 being shown. FIG. 9 is an exploded view of a customized round plate, with a side view of the assembly 900 shown in FIG. 9A. The assembly 900, which may have a diameter of 50 mm, comprises a polyacrylate (plexiglass) ring 910, a plate 912 of polyacrylate material, filter paper 914, and a bottom polyacrylate disk 916. The ring 910 may be 2-mm to ⅛ inch thick and one cm wide. The plate 912 has 4 mm or ¼ inch holes for holding gel phase chemiluminescent enzyme or immunoassay. The filter paper 914 may be cellulose acetate or cellulose nitrate. The ring 910, plate 912 and disk 916 each have four 2-mm or ⅛ inch holes for nylon or plastic screws 920.

The plate 900 or 1000 is used in a thermal control chamber as shown in FIG. 11. A black felt covered sliding plate holder 1110 has a pull 1112, an overlapping end 1114 for light seal, and retaining lips 1116. The plate holder 1110 goes into an air chamber 1120, having an inlet tube 1122 for thermoregulated air input, and an air outlet tube 1124. Thermoregulated air may be supplied to tube 1122 in a manner similar to the supply of air to tube 1189 in FIG. 12, as described below. An optical fiber light guide 1130 interfaces with the sample plate through an opening in the air chamber 1120 having a collar 1126. The light guide 1130 may be coupled to a camera as shown in FIG. 2 or FIG. 6.

Figure 12:
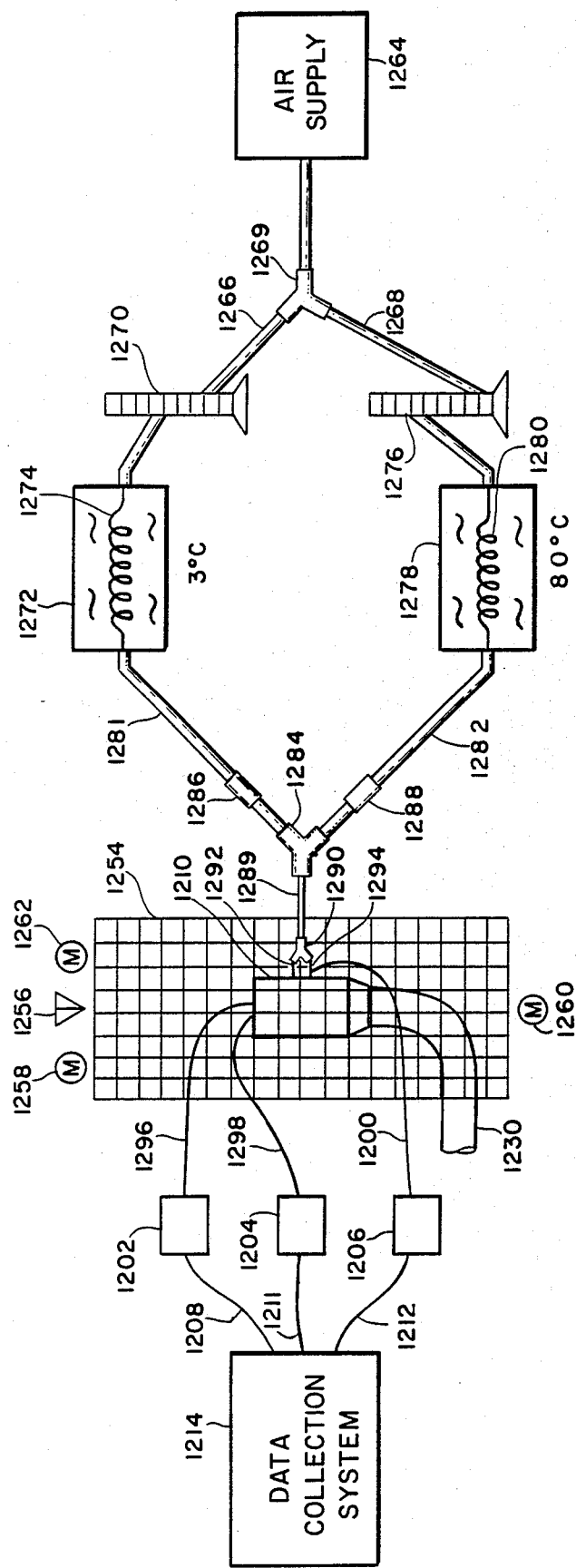
FIG. 12 is a schematic view of a circularly polarized waveguide and a thermal control system, for use with a QLIS system.

FIG. 12 is a schematic view of a circularly polarized waveguide and a thermal control system, similar to that shown in a co-pending patent application serial No. 07/056,034 filed June 1, 1987 by J. L. Kiel et al titled "Flow-Through Cell Cultivation System". modified for use with a QLIS system. A sample holder 1210 may comprise a styrofoam chamber for a microtiter plate 900 or 1000 as shown in FIG. 9 or 10; or for a flowcell holder as shown in said co-pending patent application S.N. 07/056.034.

The chamber or holder 1210 is positioned inside a circularly polarized wire cage waveguide 1254. Radiofrequency (RF) radiation is introduced by a RF power source 1256. The amount of RF radiation power present within waveguide 1254 is measured by RF power meter 1258 measuring the RF power originally entering waveguide 1254, RF power meter 1260 measuring the RF power leaving the opposite end of waveguide 1256 and RF power meter 1262 measuring the RF power reflected back out of waveguide 1254. In addition to these measurements of RF power from waveguide 1254, the heating and cooling curves from the output of the thermal probes provide a more accurate calorimetric measurement of the heat absorbed within the flowcell.

Air to be cooled or heated and then delivered to a cavity of flowcell holder 1210 is supplied from air supply 1264. The air is separated into conduits 1266 and 1268 by a Y-fitting 1269. Conduit 1266 directs air to an air flow valve and meter 1270 which controls the delivery of air to a liquid bath 1272 kept refrigerated to 3° C. A coiled copper tube 1274 increases the transfer rate of heat out of the air into liquid bath 1272 to cool the incoming air. Conduit 1268 directs air to an air flow valve and meter 1276 which controls the delivery of air to a liquid bath 1278 kept heated to 80° C. A coiled stainless steel tube 1280 increases the transfer rate of heat out of the liquid bath 1278 to heat the incoming air. Coiled tubes 1274 and 1278 may be made of any suitable material having a high rate of heat transfer. Cooled air from bath 1272 and heated air from bath 1278 are directed through respective conduits 1281 and 1282 to mix at Y-fitting 1284 to create an even temperature output of temperature controlled air through conduit 1289. Check valves 1286 and 1288 are an additional control on the delivery of air. Another Y-fitting 1290 separates the mixed air from Y-fitting 1284 into conduits 1292 and 1294 to separately enter intake ports to create the previously described turbulent flow against flowcell 1210.

Leads 1298 and 1200 from respective thermal probes are connected to respective thermal probe controllers 1202, 1204 and 206 Leads 1208, 1211 and 1212 extend to a data collection system 1214 for monitoring of air and cell bed temperatures. The thermal probes are high resistance carbon probes that do not interact with the microwave or RF radiation inside waveguide 1254. Leads 1296, 1298 and 1200 are also electromagnetically non-interactive. Vitek brand thermal probes, now available from BSD Medical Corporation, Salt Lake City. Utah, have worked successfully.

An optical fiber light guide 1230 is added to the system of FIG. 12 to interface with the sample plate through an opening in the chamber or holder 1210 in the waveguide 1254. The light guide 1230 may be coupled to a camera as shown in FIG. 2 or FIG. 6.

The Quantitative Luminescence Imaging System (QLIS) is used to assay luminescent reactions employing oxidative and peroxidative enzymes to measure the concentrations of various substrates in fluids (biological and artificial). Also, these enzymes can be conjugated with antibody specific for a given antigen in order to link the antigen with a luminescent detection reaction. Furthermore, the enzymes can be conjugated with DNA or RNA probes to detect specific nucleotide sequences.

The luminescent reactions are performed on a gel state chemiluminescent material (See 1. Kiel, J. L. Microwave Effects on Immobilized peroxidase Chemiluminescence. Bioelectromagnetics 4: 193-204 (1983); 2. Kiel, J. L. Microchemiluminescent Assay System (U.S. patent application Ser. No. 06/652,856 now abandoned); 3. Kiel, J. L., Simmons. D. M., and Erwin, D. N. Gel State Chemiluminescence: An Artificial Electron Transport System. 4th International Congress on Oxygen Radicals, 27 June-3 July 1987, University of California at San Diego, La Jolla, Calif. (Platform presentation)). This material allows for localization of the reaction so that several reactions may be run simultaneously within a field of observation. The luminescence may be initiated, enhanced and/or propagated by means of electrodiffusion. Static and radiofrequency electromagnetic fields may drive the electrodiffusion (See 4. Nussbaum, J. H., and Grodzinsky, A. J. Proton Diffusion Reaction in a Protein Polyelectrolyte Membrane and the Kinetics of Electromechanical Forces. Journal of Membrane Science 8: 193-219 (1981); 5. Grodzinsky, A. J., and Weiss, A. M. Electric Field Control of Membrane Transport and Separations. Separations and Purification Methods 14: 1-40 (1985); 6. Kiel, J. L., Wong, L.S., and Erwin, D. N. Metabolic Effects of Microwave Radiation and Convection Heating on Human Mononuclear Leukocytes. Physiological Chemistry and Physics and Medical NMR 18: 181-187 (1986)). An example of a luminescent reaction enhanced by radiofrequency radiation has been previously described (See 1. Kiel, J. L. Microwave Effects on Immobilized Peroxidase Chemiluminescence. Bioelectromagnetics 4: 193-204 (1983)). Although this previous report did not use the QLIS, it indicated that localized effects of microwave radiation on chemiluminescent reactions can occur and can by recorded on photographic film. Table 1 indicates that horseradish peroxidase (HRP), and luminol-bovine serum albumin (lu-BSA) gel specifically luminesced when exposed to a low concentration of $H_2O_2$ 3 micromoles/ml made from glucose by glucose oxidase. However, in Table 2, the increase of bulk buffer pH (a change of 4 units) did not greatly change the surface pH of activated gel (a change of 1.68). Based upon theoretical work on proton diffusion in polyanionic membranes, one would expect considerable enhancement of luminescence by an electric field (static or alternating) when a proton gradient as described above exists across a gel (See 4. Nussbaum, J. H., and Grodzinsky, A. J. Proton Diffusion Reaction in a Protein Polyelectrolyte Membrane and the Kinetics of Electromechanical Forces. Journal of Membrane Science 8: 193-219 (1981)).

Rate of heating and equilibrium temperature affect leukocyte oxidative responses that lead to chemiluminescence. (See 6. Kiel, J. L., Wong. L.S., and Erwin, D. N Metabolic Effects of Microwave Radiation and Convection Heating on Human Mononuclear Leukocytes. Physiological Chemistry and Physics and Medical NMR 18: 181-187 (1986)) Therefore, the QLIS with its accompanying rapid thermal and microwave radiation control system can take advantage of the enhancement of the gel state reactions by electromagnetic fields and the thermal effects on the chemiluminescence of leukocytes without itself being affected either by heat or electromagnetic fields.

The effects of heat and microwave radiation on chemiluminescence of red blood cells can be used as an assay for oxidative aging of red blood cells by chemical or physical stressors. (See 7. Kiel, J. L., and Erwin, D. N. Physiologic aging of mature porcine erythrocytes: Effects of various metabolites, antimetabolites, and physical stressors. American Journal of Veterinary Research 47: 2155-2160 (1986)). Oxidative aging of red blood cells is important because it is related to toxic injury, radiation injury, inborn errors of metabolism, and the half-life of red blood cells in vitro and in vivo.

Figure 13:
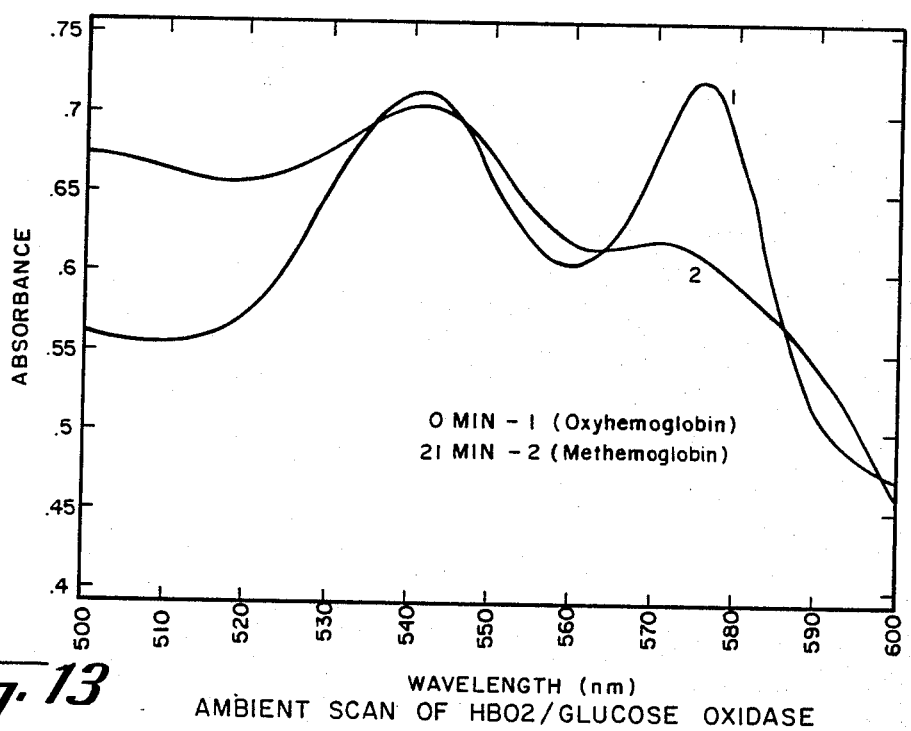
FIG. 13 is a graph of an ambient scan of HB02/Glucose Oxidase.
Figure 14:
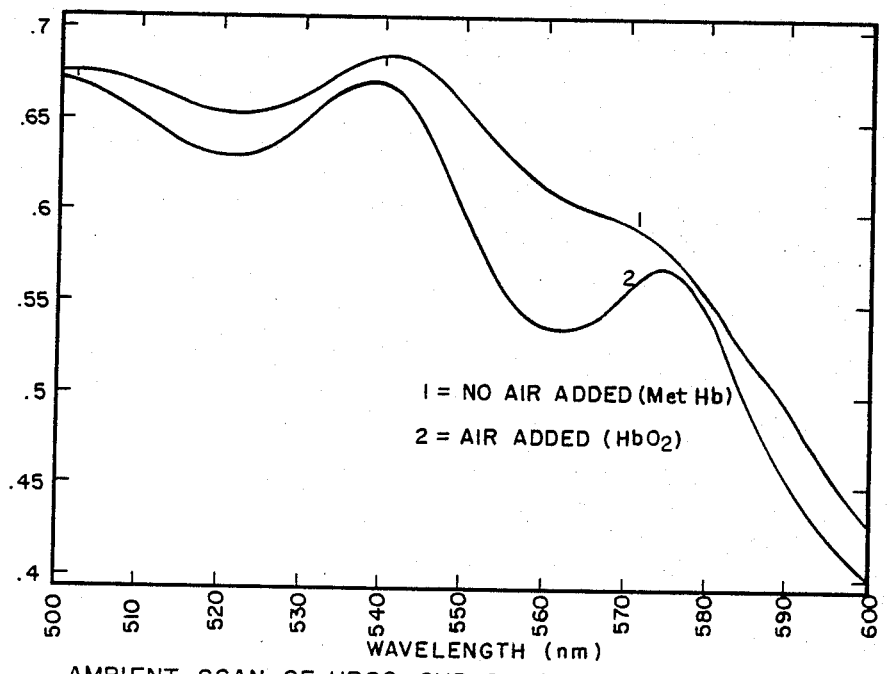
FIG. 14 is a graph of an ambient scan of HB02/GHP/Glucose Oxidase (with and without air)

The visible light absorption spectra in FIG. 13 illustrates that GO (glucose oxidase) (0.2 mg/ml), D-glucose (1 mg/ml), and ambient oxygen from air form hydrogen peroxide that, in turn, oxidizes oxyhemoglobin to methemoglobin. The visible light absorption spectra in FIG. 14 show that the addition of 100 microliters/ml of partially purified green hemoprotein (GHP) from the same blood as the oxyhemoglobin (in FIG. 13) results in the formation of oxyhemoglobin from the methemoglobin formed by the action of hydrogen peroxide from Go-D-glucose. Chemiluminescence can be used to measure the inhibition of thermally induced autoxidation of oxyhemoglobin. (See 8. Kiel, J. L., and Erwin, D. N. Thermochemiluminescent Assay of porcine, Rat, and Human Erythrocytes for Antioxidative Deficiencies. Analytical Biochemistry 143:231-236 (1984); 9. Kiel, J. L., and Erwin, D. N. Microwave Radiation Effects on the Thermally Driven Oxidase of Erythrocytes. International Journal of Hyperthermia 2: 201-212 (1986)). The microwave radiation enhancement of the inhibition of oxyhemoglobin autoxidation by GHP as measured by inhibition of chemiluminescence can also be used as a sensitive assay for GHP (see FIG. 15). Deficiency of GHP or alteration of its reaction kinetics can be an inborn error of metabolism possibly related to porcine stress syndrome, human malignant hyperthermia, or chronic granulomatous disease. Furthermore, types of hemoglobin that abnormally interact with GHP can be detected by kinetic changes in the thermally induced autoxidation reaction measured by chemiluminescence (see FIG. 15).

Specific examples of the application of the QLIS to enzymatic, immunological, and nucleic acid chemiluminescent assays are described as follows:

1. Glucose detection. Chemiluminescent gel is prepared by mixing 1 mg GO, 1 mg HRP and 30 mg Lu-BSA per ml of pH6.9 sodium phosphate(0.01M) buffered saline (0.154M). The Lu-BSA is prepared by adding 1 mg luminol per ml of the above mixture in sodium phosphate (0.01M) buffered saline (0.154M) (PBS) and filtering it with a 0.22 micrometer (pore size) filter. The filtrate should be clear. To the filtrate is added enough glutaraldehyde to produce a final concentration of 0.5% (volume/Volume). Twenty-five microliters of the solution is added to each 7-mm filter paper disk in each well of a standard flat bottom microtiter plate 1000 (24, 46, or 96 Wells) as shown in FIG. 10 or a customized round plate 900 like that illustrated in FIG. 9. The gel is allowed to form and attach the paper to the plastic substrata. The gel formation may be stopped by the addition of 100 microliters of 0.01M sodium metabisulfite or ammonium carbonate in water to each disk. The disks are washed three times with distilled water pipetted into and out of the wells. The plates are kept covered with opaque material such as aluminum foil in the refrigerator (4C) to maintain moisture and block out light until they are used. The disks give the best results if used 48 hours after preparation. To test for glucose, the solution suspected of containing glucose is added to each disk in 200 microliter volumes. Standards of known glucose concentration are added to control disks. The plate containing activated disks is placed in the thermal control chamber, and the luminescence is recorded by the QLIS though its fiberoptic system as shown in FIG. 11. The luminescence may be activated at a suboptimal pH such as 6.0, 7.0, or 7.4 (see Table 1, FIG. 15). The gel is then placed in a waveguide and exposed to microwave radiation (2450 MHz, 100 to 120 W/kg) at a fixed temperature (25, 30, 37, 40, or 45° C.) to enhance the reaction in a highly controlled manner that reduces variability (FIG. 12). For a complete description of the thermal control and microwave system see said co-pending patent application Ser. No. 07/056,034 for a Flow-Through Cell Cultivation System. In the case of a microtiter assay the long axis of the waveguide is placed vertical to prevent spillage of plate contents during exposure.

2. *Campylobacter pylori* (pyloridis) antibody assay. *Campylobacter pylori* is strongly associated with chronic gastric and peptic ulcer in humans. (See 10. Marshall, B. J., Royce, H., Annear, D. I., et al. Original isolation of *Campylobacter pyloridis* from human gastric mucosa. Microbios 25: 83-88 (1984); 11. Price, A. B., Levi, J., Dolby, J. M., et al. *Campylobacter pyloridis* in peptic ulcer disease: Microbiology, pathology, and scanning electron microscopy. Gut 26: 1183-1188 (1985)). Unfortunately, stomach biopsy is necessary for obtaining material for culture and identification of the organism by standard microbiological techniques. Enzyme linked immunoassays (ELISA) have been developed for determining infection by the presence of antibody titers to the organism in patients' sera. One such assay was 97% specific and 81% sensitive (See 12. Goodwin, C. S., Blincow, E., Peterson, G., et al. Enzyme-linked Immunosorbent Assay for *Campylobacter Pyloridis:* Correlation with Presence of *C. Pyloridis* in the Gastric Mucosa. The Journal of Infectious Diseases 155: 488-494 (1987)).

A luminescent immunoassay (LIA) for this infection has not been previously developed. The LIA for use in the QLIS is composed of a crosslinked gel made like the one in example 1 except that the GO is omitted and $10^4$ to $10^6$ heat-killed (62C in distilled water for 1 hour) *Campylobacter pylori* organisms are included in the gel. Heat-inactivated serum from the patient made up into various dilutions with 0.01M TRIS (pH 8.0) or PBS (pH 7.4) is added in 200 microliter aliquots to the disks in the microtiter plate and allowed to incubate at 37C for 30 minutes. The free serum is then washed out of the plates by pipetting in and out pH 7.4 PBS 3 times. Next, 200 microliters of 1 to 10 micrograms/ml PBS pH 7.4 of antihuman IgG antibody conjugated with GO is added to each disk and incubated for 30 minutes at 37C. Free antibody is washed from the disks as was the patient's serum. Glucose solution (200 microliters of at least 1 mg/ml) is PBS pH 7.4 is added next to the disks, they are placed in a QLIS (FIG. 11). and the chemiluminescence is read at 37C and 100 to 120 W/kg 2450 MHz microwave radiation or at an optimal temperature and power determined by running known positive serum.

3. Indirect luminescent immunoassay for cachectin (tumor necrosing factor). Cachectin, tumor necrosing factor, is difficult to assay because the assays require either cells in culture or mice for toxicity measurements. Circulating levels of the monokine in animals and humans with cachexia may be below the level of sensitivity for these assays. (See 13. Beutler, B., and Cerami, A. Cachectin: More than a Tumor Necrosis Factor. The New England Journal of Medicine 316: 379-385 (1987)). Therefore, a sensitive, economical, rapid assay for cachectin would be very useful.

The LIA for cachectin involves incorporating 1 to 10 micrograms of purified cachectin into crosslinked Lu-BSA gels in paper disks like those described in the previous examples An antibody against cachectin is produced in rabbits and used at a concentration (in pH 8.0 TRIS saline or pH 7.4 PBS) necessary to just saturate the disk bound cachectin. The sample of serum or extracellular fluid containing an unknown concentration of cachectin is added to free antibody to the cachectin. This solution is incubated at 37C for 30 minutes. Then, it is added to disks containing immobilized cachectin and further incubated for 30 minutes at 37C. The disks are then washed as described in the campylobacter LIA. A second antibody against the rabbit antibody conjugated with GO is added to the disks at a concentration that saturates the binding sites on all the rabbit antibody that can be attached to the bound cachectin. The disks would then be washed three times as before. The glucose activation and the QLIS (FIG. 11) are used as in the campylobacter LIA. Fluid samples containing known concentrations of cachectin are used to standardize the luminescent response in respect to cachectin concentration.

4. Oxidative cellular assay for monocytes, macrophages, granulocytes (neutrophils, eosinophils, mast cells, and basophils), Langerhans cells, keratinocytes, uterine epithelial cells, dendritic cells, gastrointestinal lYmphoid and epithelial cells, platelets, endothelial cells qlial cells and placental cells. The basic assay is composed of a qlutaraldehyde crosslinked Lu-BSA and HRP gel like that in the above examples (without GO, cachectin, or campylobacter antigen). Antibody against BSA is added to the gel disks in pH 8.0 TRIS saline or pH 7.4 PBS at a concentration between 1 and 100 micrograms/ml, inclusive and incubated for 30 minutes at 37C. Free antibody is washed away by pipettinq fresh buffer into and out of the plate as described in previous examples. A 200 microliter aliquot of cell suspension prepared from $10^4$ to $10^6$ cells in Hank's balanced salt solution without phenol red and containing 20 mM pH 7.4 HEPES buffer is added to each disk The cells and disk are incubated at room temperature for 20 minutes and then placed in the microwave and thermal control chamber connected to the QLIS (FIG. 6 ) and brought up to 37C. The chemiluminescence measured versus time is an indication of oxidative response to antigen-/antibody complexes. Other antigens, hormones, or cytokines can be added to the gel to bind and oxidatively activate cells. Lectins such as Conoanavalin A (Con a) or phytohemagglutinin (PHA) can be crosslinked in the gel, substituting for the antibody/antigen complex, to bind cells such as lymphocytes.

5. Red blood cell (RBC) assay for autoantibody. Autoantibody binds to RBCs in autoimmune hemolytic anemia, following chemical or radiation damage, and with aging of RBCs. In this LIA, 100 microliters of whole fresh blood with heparin as an anticoagulant is added to a gel (filter paper) disk containing crosslinked Lu-BSA, and Con A, PHA, wheat germ agglutinin, or anti-RBC antibody The disks are incubated for 30 minutes at 37C in a humidified chamber and then washed three times with pH 7.4 PBS to remove unbound RBCs. Two hundred microliters of HRP conjugated antibody (1 to 100 micrograms/ml) against the antibody of the species from which the RBCs were taken is added to the disk with bound RBCs and the preparation is incubated for one hour at 37C. Free conjugated antibody is removed from the disks by gentle washing with buffer as described in the previous examples. Disks are activated with 200 microliters 4.4 mM $H_2O_2$ in PBS pH7.4 and the chemiluminescence measured by the QLIS (FIG. 6) as described for the other examples. The chemiluminescence increases with increasing autoantibody on the RBCs.

6. Assay for red blood cell green hemoprotein (GHP). RBCs or whole blood preparations are lysed by dilution to 1:1000 in distilled water and 200 microliters of the hemolysate is crosslinked by glutaraldehyde (0.5%) with Lu-BSA (30 mg/ml) in filter paper disks (7 mm) in a similar fashion to the crosslinked gels described in the previous examples. The disks are activated by adding 200 microliters of PBS pH 7.4 containing 4.4 mM $H_2O_2$ in 0.1 N NaOH. The luminescence of control disks (without GHP, methemoglobin only) is compared to that of disks with GHP at temperatures of 20–40° C. with or without microwave radiation (2450 MHz, 50 to 120 W/kg). (Using the QLIS of FIG. 11). FIG. 15 illustrates some example results.

7. Use of luminescent biotinylated nucleic acid probes to look at the expression of nucleic acids after exposure of cells to microwave radiation. DNA fragments chosen as probes (such as those for but not limited to cachectin, tumor necrosing factor interleukin 1, and interleukin 2) are nicked with DNA polymerase I-DNAse I and in the repair process incorporate biotinylated dUTP (deoxyuridine triphosphate) in place of dTTP (deoxythymidine triphosphate). (see 14. Kelly, R. B., Cozzarelli, N. R., Deutscher, M. P., Lehman, I. R., and Kornberg, A. Enzymatic Synthesis of Deozyribonucleic Acid. XXXII. Replication of Duplex Deoxyribonucleic Acid by Polymerase at a Single Strand Break. The Journal of Biological Chemistry 245: 39–45 (1970); 15. Manitis, T., Jeffrey. A., and Kleid, D. G. Nucleotide Sequence of the Rightward Operator of Phage. The Proceedings of the National Academy of Sciences of the United States of America 72: 1184–1188 (1975); 16. Rigby, P. W. J., Dieckmann, M., Rhodes, C., and Berg, P. Labeling Deoxyribonucleic Acid to High Specific Activity in Vitro by Nick Translation with DNA Polymerase I. Journal of Molecular Biology 113: 237–251 (1977)). The enzymes (Nick Translation Reagent Kit. 81605B) and biotinylated dUTP (Blugene. Nonradioactive Nucleic Acid Detection System) are obtained from Bethesda Research Labs, Gaithersburg, MD 20877. Labelling DNA probes with the random prime method can also be used with biotinylated nucleotides. (See 17. Feinberg. A. P., and Vogelstein, B. A. Technique for Radiolabelling DNA Restriction Endonuclease Fragments to High Specific Activity. Analytical Biochemistry 132: 6–13 (1983)). Oligonucleotides (6 nucleotides long) serve as primers for copying single stranded DNA templates in the presence of the Klenow fragment.

The hybridization requires 200 nanograms/ml of biotinylated label in the final hybridization solution. After preparation of the probes. DNA or RNA to be tested that has been extracted from microwave exposed cells is either blotted by Southern blot technique from electrophoresed gels or dot blotted onto nitrocellulose or nylon membranes and prehybridized and hybridized. Hybridization solution contains sodium dodecyl sulfate, salmon sperm DNA, dextran sulfate (optional), sodium phosphate, sodium chloride, EDTA in Denhardt's solution, formamide, and the probe. The reaction is carried out at 42C. After washing, the filters are processed for chemiluminescence.

Streptavidin or avidin HRP, methemoglobin, or GHP conjugates (prepared by crosslinking with 0.2% glutaraldehyde) are allowed to combine with the biotinylated probes attached to DNA or RNA on the filters in PBS pH 7.4 for 30 minutes at 37C. Free HRP, methemoglobin, or GHP conjugate is washed away with PBS pH 7.4. The filter and bound DNA/DNA or RNA is overlaid with a thin layer (1 mm or less) of chemiluminescent solution composed of 30 mg/ml Lu-BSA, and 0.5% glutaraldehyde in PBS pH 6.9. The solution is allowed to gel at room temperature for 30 minutes to 1 hour. The gel is activated by the addition of 200 to 500 microliters of 4.4mM $H_2O_2$ solution in 0.1 N NaOH. Chemiluminescence is measured with the QLIS (FIG. 12) as described in the other examples and is proportional to the amount of bound probe.

It is understood that certain modifications to the invention as described may be made, as might occur to one with skill in the field of the invention, within the scope of the appended claims. Therefore, all embodiments contemplated hereunder which achieve the objects of the present invention have not been shown in complete detail. Other embodiments may be developed without departing from the scope of the appended claims.

TABLE 1

Chemiluminescence (Relative light units/45 secs ± S.D. after 6 min) of Crosslinked Glucose Oxidase, Horseradish Peroxidase, and Bovine Serum Albumin (IC-1) or Luminol-Bovine Serum Albumin (IC-1L).

| pH* | IC-1 | IC-1L |
|---|---|---|
| 6.0 | 0.365 ± 0.0146 (n = 5) | 6.851 ± 0.862 (n = 6) |
| 6.5 | 0.370 ± 0.0204 (n = 5) | 16.76 ± 1.778 (n = 7) |
| 7.0 | 1.283 ± 0.102 (n = 5) | 112.4 ± 1.329 (n = 6) |
| 7.4 | 1.477 ± 0.181 (n = 4) | 348.7 ± 11.57 (n = 7) |
| 7.4 (no glucose) | | 0.0078 ± 0.0055 (n = 5) |
| 8.0 | 1.773 ± 0.337 (n = 4) | 1998.0 ± 228.5 (n = 6) |
| 8.0 (no glucose) | | 0.4865 ± 0.008 (n = 6) |
| 10.0 | 1.045 ± 0.068 (n = 4) | 2397.0 ± 197.0 (n = 7) |
| 10.0 (no glucose) | | 0.8265 ± 0.011 (n = 6) |

*The buffer was phosphate buffered saline (0.01 M sodium phosphate and 0.154 M NaCl) with 0.5 mg/ml D-glucose; at pH 8.0 and 10.0 the PBS pH was adjusted with 0.01 M sodium carbonate.

TABLE 2

BUFFERING CAPACITY AND PROTON EXCHANGE BY IC-IL GEL

| | Bulk Buffer pH | | Gel Surface pH | |
|---|---|---|---|---|
| Starting | After Gel[a] | After Gel + Glucose[b] | Without Glucose | With Glucose |
| | | | 5.22 ± 0.025 (n = 4)[c] | |
| 7.4 | 7.61 ± 0.04 (n = 4) | 7.66 ± 0.05 (n = 4) | 6.11 ± 0.07 (n = 8) | 5.42 ± 0.09 (n = 4) |
| 10.0 | 9.09 ± 0.12 (n = 3) | 9.12 ± 0.12 (n = 3) | 6.98 ± 0.02 (n = 3) | 6.90 ± 0.03 (n = 3) |

[a]200 μl buffer (0.01 M PBS at pH 7.4 or 0.01 M TRIS/Saline at pH 10.0) added to 7 mm paper disks containing 25 μl of gel each.
[b]Same as [a] except the buffer contained 0.5 mg D-glucose/ml.
[c]Mean ± 1 standard deviation of number of disks in parentheses.

What is claimed is:

1. A quantitative luminescence imaging system (QLIS) comprising a sample excitation unit which includes excitation means for exciting a sample by irradiation in an RF field to produce a luminescent reaction, video camera means, image transfer optic means arranged for coupling light from said sample to an input of the video camera means, the light being converted in the video camera means to electronic signals at an output thereof, and an electronic data processing system coupled to the output of the video camera means for processing the signals, the image transfer optic means being arranged so that the input of the video camera means is outside of the environment of said excitation means.

2. A quantitative luminescence imaging system according to claim 1, which is a macroscopic system, wherein the sample excitation unit comprises an RF waveguide having a sample chamber for said sample, the video camera is a low light level camera, and the data processing system comprises an image processor and a control computer.

3. A quantitative luminescence imaging system according to claim 2.
wherein the image transfer optics is a bundle of optic fibers having a bend; and
wherein the video camera means comprises a microchannel plate image intensifier optically coupled to a video camera tube, with the image intensifier comprising a fiber optic faceplate for the light input, a photocathode, focusing electrodes, microchannel plates, and a phosphor screen for the light output.

4. A quantitative luminescence imaging system according to claim 1, which is a microscopic system, wherein the sample excitation unit comprises an RF antenna/sample holder at the end of an RF transmission line, the excitation means being an RF field at the RF antenna/sample holder when an RF signal is supplied via the transmission line, the image transfer optics is a microscope having the sample holder located at the normal specimen point in the light path of the microscope, and the video camera means is a low light level camera attached to the microscope.

5. A quantitative luminescence imaging system (QLIS) comprising a sample excitation unit which includes excitation means for exciting a sample by microwave radiation as an activator to produce a luminescent reaction, video camera means, image transfer optic means arranged for coupling light from said sample to an input of the video camera means, the light being converted in the video camera means to electronic signals at an output thereof, and an electronic data processing system coupled to the output of the video camera means for processing the signals, the image transfer optic means being arranged so that the input of the video camera means is outside of the environment of said excitation means.

* * * * *

UNITED STATES PATENT AND TRADEMARK OFFICE
CERTIFICATE OF CORRECTION

Page 1 of 3

PATENT NO. : 4,948,975

DATED : August 14, 1990

INVENTOR(S) : David N. Erwin et al

It is certified that error appears in the above-identified patent and that said Letters Patent is hereby corrected as shown below:

```
IN THE ABSTRACT, line 8, "process or" should read --processor--.
Col 1, line  9, "aWarded" should read --awarded--.
Col 1, line 11, "qovernmental" should read --governmental--.
Col 1, line 39, a period should follow "photons".
Col 1, line 50, a period should follow "emissions".
Col 1, line 52, "video" should read --vidicon--.
Col 2, line 14, a period should follow "field".
Col 2, line 41, the third occurrence of "3a" should read --3b--.
Col 3, line  9, a period should follow "room".
Col 3, line 12, "Immobilized" should read --Immobilized--.
Col 3, line 20, a period should follow "system".
Col 3, line 26, a colon should follow "8".
Col 3, line 32, a period should follow "Leukocytes" and
"physiological" should be capitalized.
Col 3, line 37, a period should follow "stressors".
Col 3, line 38, a colon should follow "47".
Col 3, line 39, a period should follow "N".
Col 3, line 50, after "74", insert --(Nov. -Dec. 1979).--."
Col 3, line 51, a period should follow the first occurrence of "J".
Col 3, line 55, a period should follow both "S" and "G".
Col 3, line 58, a period should follow "Mucosa".
Col 3, line 59, a period should follow "(1987)".
Col 3, line 61, a period should follow "Factor".
Col 4, line  8, a comma should follow "113".
Col 4, line 10, the period following "A" should be deleted.
Col 4, line 24, a period should follow "reaction".
Col 4, line 44, "With" should read --with--.
```

UNITED STATES PATENT AND TRADEMARK OFFICE
CERTIFICATE OF CORRECTION

PATENT NO. : 4,948,975

DATED : August 14, 1990

INVENTOR(S) : David N. Erwin et al

It is certified that error appears in the above-identified patent and that said Letters Patent is hereby corrected as shown below:

```
Col  4, line 60, "shoWn" should read --shown--.
Col  5, line  1, "wavequide" should read --waveguide--.
Col  5, line 15, a comma should follow "slide".
Col  5, line 19, a period should follow "380".
Col  5, line 20, "remoVable" should read --removable--.
Col  5, line 44, "3a" should read --3b--.
Col  5, line 61, "imaginq" should read --imaging--.
Col  5, line 68, a period should follow "sufficient".
Col  7, line 12, a period shouold follow "bus".
Col  7, line 23, a period should follow "Corp.)".
Col  7, line 27, a period should follow "Corp".
Col  7, line 54, a comma should follow "601".
Col  7, line 54, "loWer" should read --lower--.
Col  7, line 60, a comma should follow "601".
Col  7, line 66, --inches-- should precede "high".
Col  8, line 13, a comma should follow "thick)".
Col  8, line 68, a period should follow "VMS".
Col  9, line 22, "processing" should be capitalized.
Col  9, line 45, "th" should read --the--.
Col  9, line 53, the period should be a comma.
Col 10, line 64, "056.034" should read --056,034--.
Col 11, line 36, --1296-- should precede "1298".
Col 11, line 38, "206" should read --1206--.
Col 11, line 45, the period should be a comma.
Col 11, line 65, "peroxidase" should be capitalized.
Col 12, line 50, a period should follow "N".
Col 13, line 17, "porcine" should be capitalized.
Col 13, line 49, "Wells" should read --wells--.
```

UNITED STATES PATENT AND TRADEMARK OFFICE
CERTIFICATE OF CORRECTION

PATENT NO. : 4,948,975

DATED : August 14, 1990

INVENTOR(S) : David N. Erwin et al

It is certified that error appears in the above-identified patent and that said Letters Patent is hereby corrected as shown below:

```
Col 13, line 49, "shoWn" should read --shown--.
Col 13, line 67, "shoWn" should read --shown--.
Col 14, line 14, "ulcer" should read --ulcers---.
Col 14, line 15, a period should follow "J".
Col 14, line 50, the first occurrence of "is" should read --in--.
Col 15, line  1, a period should follow "examples".
Col 15, line 25, "lYmphoid" should read --lymphoid--.
Col 15, line 26, "qlial" should read --glial--.
Col 15, line 27, "qlutaraldehyde" should read --glutaraldehyde--.
Col 15, line 33, "pipettinq" should read --pipetting--.
Col 15, line 38, a period should follow "disk".
Col 15, line 46, "Conoanavalin" should read --Concanavalin--.
Col 15, line 57, a period should follow "antibody".
Col 16, line 55, the period should be a comma.
```

Signed and Sealed this

Twenty-sixth Day of January, 1993

*Attest:*

DOUGLAS B. COMER

*Attesting Officer*   *Acting Commissioner of Patents and Trademarks*